US012349942B2

(12) United States Patent
Josse et al.

(10) Patent No.: US 12,349,942 B2
(45) Date of Patent: Jul. 8, 2025

(54) SURGICAL SYSTEM AND METHOD

(71) Applicant: Warsaw Orthopedic, Inc., Warsaw, IN (US)

(72) Inventors: Loic Josse, Palm Beach Garden, FL (US); Bertrand Peultier, Les Hopitaux Neufs (FR)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 114 days.

(21) Appl. No.: 17/606,013

(22) PCT Filed: Apr. 23, 2019

(86) PCT No.: PCT/US2019/028632
§ 371 (c)(1),
(2) Date: Oct. 22, 2021

(87) PCT Pub. No.: WO2020/219020
PCT Pub. Date: Oct. 29, 2020

(65) Prior Publication Data
US 2022/0202450 A1 Jun. 30, 2022

(51) Int. Cl.
*A61B 17/88* (2006.01)
*A61B 17/70* (2006.01)
*A61B 17/02* (2006.01)

(52) U.S. Cl.
CPC ...... *A61B 17/7032* (2013.01); *A61B 17/7077* (2013.01); *A61B 2017/0256* (2013.01)

(58) Field of Classification Search
CPC . A61B 17/68; A61B 17/7077; A61B 17/7079; A61B 17/708; A61B 2017/025
(Continued)

(56) References Cited

U.S. PATENT DOCUMENTS 6,030,402 A 2/2000 Thompson et al.
6,139,493 A 10/2000 Koros et al.
(Continued)

FOREIGN PATENT DOCUMENTS

CN 101489497 A 7/2009
CN 108498152 A 9/2018
(Continued)

OTHER PUBLICATIONS

European Patent Office, 80298 Munich, Germany, Extended European Search Report, EP Application No. 19925589.4, PCT/US2019028632, Date of mailing: Nov. 7, 2022.
(Continued)

*Primary Examiner* — Eduardo C Robert
*Assistant Examiner* — David C Comstock
(74) *Attorney, Agent, or Firm* — Sheridan Ross P.C.

(57) ABSTRACT

A surgical compression instrument includes a member configured for disposal longitudinally along a first implant support for pivotably connecting the first implant support with a second implant support. The first implant support is engageable with a first receiver of a first fastener having a first shaft fixed with vertebra tissue and the second implant support is engageable with a second receiver of a second fastener having a second shaft fixed with vertebral tissue. A part is movable relative to the member and engageable with the implant supports such that the second implant support moves relative to the first implant support to compress the vertebral tissue. Surgical systems, constructs, implants and methods are disclosed.

20 Claims, 11 Drawing Sheets

(58) Field of Classification Search
USPC ... 606/246, 264–267, 278, 279, 90, 99, 104, 606/105, 86 A
See application file for complete search history.

(56) References Cited

U.S. PATENT DOCUMENTS

| | | | |
|---|---|---|---|
| 8,974,497 | B2 | 3/2015 | Cho et al. |
| 9,402,660 | B2 | 8/2016 | Brinkman et al. |
| 10,314,620 | B2 | 6/2019 | Cho et al. |
| 11,576,727 | B2 | 2/2023 | Turner et al. |
| 12,114,845 | B2 | 10/2024 | Josse et al. |
| 2006/0084844 | A1 | 4/2006 | Nehls |
| 2007/0208227 | A1 | 9/2007 | Smith et al. |
| 2008/0140129 | A1* | 6/2008 | Dalton ............... A61B 17/7059 606/279 |
| 2010/0069976 | A1 | 3/2010 | de Villiers et al. |
| 2012/0296172 | A1 | 11/2012 | Raven, III et al. |
| 2012/0316609 | A1 | 12/2012 | Wall et al. |
| 2013/0310942 | A1 | 11/2013 | Abdou |
| 2014/0024900 | A1 | 1/2014 | Capote et al. |
| 2014/0066718 | A1 | 3/2014 | Fiechter et al. |
| 2014/0107656 | A1 | 4/2014 | Masson et al. |
| 2014/0257044 | A1 | 9/2014 | Blain et al. |
| 2014/0257312 | A1* | 9/2014 | Solitario, Jr. ...... A61B 17/7079 606/90 |
| 2014/0350347 | A1 | 11/2014 | Karpowicz et al. |
| 2015/0045834 | A1 | 2/2015 | McBride |
| 2015/0164569 | A1 | 6/2015 | Reitblat et al. |
| 2015/0351738 | A1 | 12/2015 | Perrow |
| 2016/0074029 | A1 | 3/2016 | O'Connell et al. |
| 2016/0089188 | A1 | 3/2016 | McBride, Jr. et al. |
| 2016/0166335 | A1 | 6/2016 | Roger et al. |
| 2016/0206442 | A1 | 7/2016 | Dvorak et al. |
| 2016/0345952 | A1 | 12/2016 | Kucharzyk et al. |
| 2017/0035406 | A1 | 2/2017 | Abidin et al. |
| 2017/0100116 | A1 | 4/2017 | Erramilli et al. |
| 2017/0112539 | A1 | 4/2017 | Hayes |
| 2017/0119449 | A1* | 5/2017 | Jones ................ A61B 17/7032 |
| 2017/0215856 | A1 | 8/2017 | Martinelli et al. |
| 2017/0252107 | A1 | 9/2017 | Jones et al. |
| 2017/0258502 | A1 | 9/2017 | Abdou |
| 2017/0311985 | A1 | 11/2017 | Bobbitt et al. |
| 2018/0042594 | A1 | 2/2018 | Miles et al. |
| 2018/0161101 | A1 | 6/2018 | Barsoum et al. |
| 2018/0289363 | A1 | 10/2018 | Barnes et al. |
| 2018/0303473 | A1 | 10/2018 | Spann et al. |
| 2018/0303552 | A1 | 10/2018 | Ryan et al. |
| 2019/0021716 | A1 | 1/2019 | Waugh et al. |
| 2019/0038366 | A1 | 2/2019 | Johnson et al. |
| 2019/0046239 | A1 | 2/2019 | Bobbitt et al. |
| 2019/0069956 | A1 | 3/2019 | Ryan et al. |
| 2019/0090864 | A1 | 3/2019 | Medeiros et al. |
| 2019/0090979 | A1 | 3/2019 | Medeiros et al. |
| 2019/0110785 | A1 | 4/2019 | Serokosz et al. |
| 2019/0216453 | A1 | 7/2019 | Predick et al. |
| 2019/0223854 | A1 | 7/2019 | Baudouin et al. |
| 2020/0054361 | A1 | 2/2020 | Peultier et al. |
| 2020/0085500 | A1 | 3/2020 | Dace et al. |
| 2022/0192645 | A1 | 6/2022 | Peultier et al. |
| 2022/0202405 | A1 | 6/2022 | Josse et al. |
| 2022/0218417 | A1 | 7/2022 | Josse et al. |
| 2023/0059813 | A1 | 2/2023 | Josse et al. |

FOREIGN PATENT DOCUMENTS

| | | |
|---|---|---|
| CN | 110381866 | 10/2019 |
| EP | 3331421 | 6/2018 |
| EP | 3351185 | 7/2018 |
| GB | 2528416 | 1/2016 |
| KR | 101446620 B1 | 9/2009 |
| WO | 1990002527 A1 | 3/1990 |
| WO | WO 2007/087536 | 8/2007 |
| WO | WO 2018/150214 | 8/2018 |
| WO | WO 2018/150215 | 8/2018 |
| WO | WO 2020/219016 | 10/2020 |
| WO | WO 2020/219018 | 10/2020 |
| WO | WO 2020/219019 | 10/2020 |
| WO | WO 2020/219020 | 10/2020 |
| WO | WO 2021/206723 | 10/2020 |

OTHER PUBLICATIONS

International Search Report for PCT/US2019/028632 date of completion is Feb. 21, 2020 (2 pages).
China Office Action: China National Intellectual Property Administration: Search Report: Application/Patent No. 201980095623.2:Jan. 23, 2024.
CN101489497A—English Translation.
CN108498152A—English Translation.
Official Action for China Patent Application No. 202080099220.8, dated Nov. 8, 2024, 10 pages.
Official Action for U.S. Appl. No. 17/795,152, dated Nov. 26, 2024, 9 pages.
Notice of Allowance for U.S. Appl. No. 17/606,011, dated Dec. 5, 2024, 8 pages.
International Search Report and Written Opinion for International (PCT) Patent Application No. PCT/US2019/028612, dated Feb. 21, 2020, 7 pages.
International Preliminary Report on Patentability for International (PCT) Patent Application No. PCT/US2019/028612, dated Sep. 28, 2021, 6 pages.
Extended European Search Report for Europe Patent Application No. 19925665.2, dated Nov. 4, 2022, 10 pages.
International Search Report and Written Opinion for International (PCT) Patent Application No. PCT/US2019/028615, dated Feb. 21, 2020, 8 pages.
International Preliminary Report on Patentability for International (PCT) Patent Application No. PCT/US2019/028615, dated Feb. 21, 2020, 7 pages.
Extended European Search Report for Europe Patent Application No. 19926119.9, dated Nov. 3, 2022, 9 pages.
Official Action for China Patent Application No. 201980095607.3, dated Jan. 25, 2024, 2 pages.
International Search Report and Written Opinion for International (PCT) Patent Application No. PCT/US2020/027533, dated Jul. 6, 2020, 8 pages.
International Preliminary Report on Patentability for International (PCT) Patent Application No. PCT/US2020/027533, dated Oct. 6, 2022, 7 pages.
Extended European Search Report for Europe Patent Application No. 20930065.6, dated Mar. 13, 2024, 5 pages.
International Search Report and Written Opinion for International (PCT) Patent Application No. PCT/US2019/028624, dated Feb. 21, 2020, 9 pages.
International Preliminary Report on Patentability for International (PCT) Patent Application No. PCT/US2019/028624, dated Sep. 28, 2021, 7 pages.
Extended European Search Report for Europe Patent Application No. 19925802.1, dated Nov. 8, 2022, 10 pages.
Official Action for Europe Patent Application No. 19925802.1, dated Jul. 18, 2024, 3 pages.
International Search Report and Written Opinion for International (PCT) Patent Application No. PCT/US2019/028628, dated Feb. 21, 2020, 7 pages.
International Preliminary Report on Patentability for International (PCT) Patent Application No. PCT/US2019/028628, dated Sep. 28, 2021, 6 pages.
Extended European Search Report for Europe Patent Application No. 19925884.9, dated Nov. 8, 2022, 11 pages.
Official Action for China Patent Application No. 201980095615.8, dated Jan. 23, 2024, 2 pages.
International Preliminary Report on Patentability for International (PCT) Patent Application No. PCT/US2019/028632, dated Sep. 28, 2021, 6 pages.
Official Action for U.S. Appl. No. 17/605,819, dated Feb. 15, 2024, 10 pages.

(56) References Cited

OTHER PUBLICATIONS

Official Action for U.S. Appl. No. 17/605,819, dated Jul. 22, 2024, 12 pages.
Official Action for U.S. Appl. No. 17/605,819, dated Sep. 27, 2024, 13 pages.
Official Action for U.S. Appl. No. 17/606,010, dated Dec. 20, 2023, 16 pages.
Notice of Allowance for U.S. Appl. No. 17/606,010, dated Jul. 9, 2024, 5 pages.
Corrected Notice of Allowance for U.S. Appl. No. 17/606,010, dated Jul. 29, 2024, 2 pages.
Notice of Allowance for U.S. Appl. No. 17/606,010, dated Sep. 16, 2024, 5 pages.
Official Action for U.S. Appl. No. 17/606,011, dated Jan. 18, 2024, 9 pages.
Official Action for U.S. Appl. No. 17/606,011, dated Jul. 3, 2024, 11 pages.
Article 94(3) Communication for Europe Patent Application No. 19925665.2, dated Dec. 17, 2024, 8 pages.
Official Action for U.S. Appl. No. 17/605,779, dated Jan. 21, 2025, 15 pages.
Notice of Allowance for U.S. Appl. No. 17/605,819, dated Jan. 23, 2025, 8 pages.

* cited by examiner

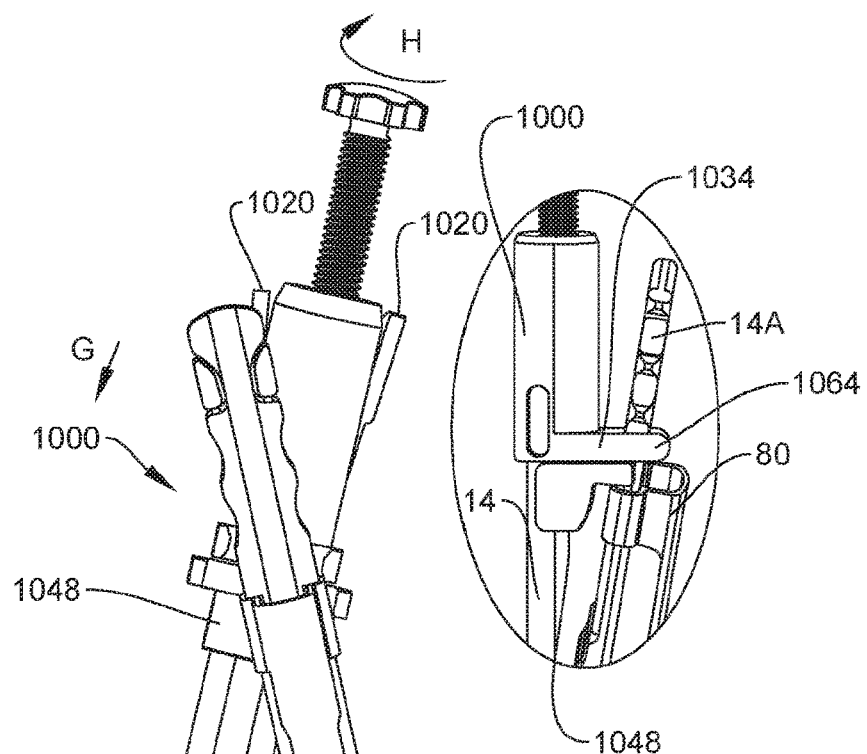
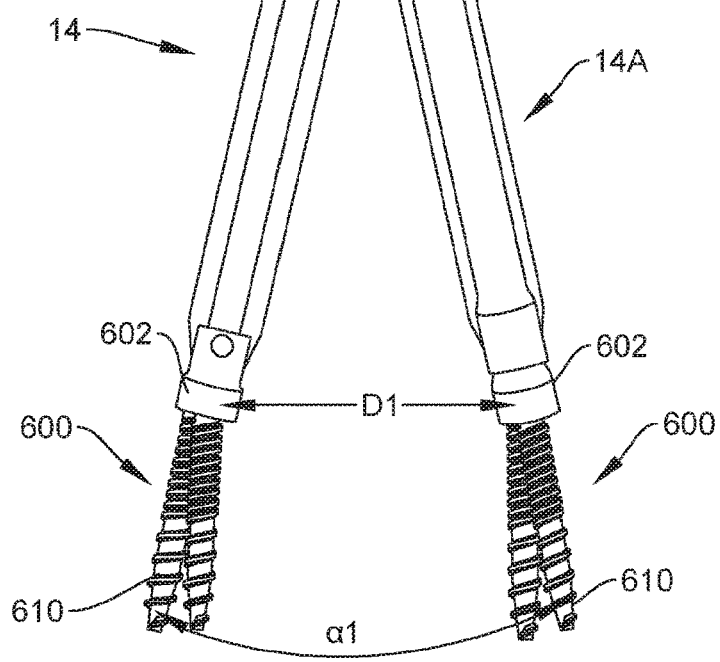
FIG. 10
FIG. 9

SURGICAL SYSTEM AND METHOD

CROSS-REFERENCE TO RELATED APPLICATIONS

This application is a National Stage Application of PCT/US2019/028632 filed Apr. 23, 2019, and the disclosure of the above-identified application is hereby incorporated by reference in its entirety.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In one embodiment, a surgical compression instrument is provided. The surgical compression instrument includes a member configured for disposal longitudinally along a first implant support for pivotably connecting the first implant support with a second implant support. The first implant support is engageable with a first receiver of a first fastener having a first shaft fixed with vertebral tissue and the second implant support is engageable with a second receiver of a second fastener having a second shaft fixed with vertebral tissue. A part is movable relative to the member and engageable with the implant supports such that the second implant support moves relative to the first implant support to compress the vertebral tissue. In some embodiments, surgical systems, constructs, implants and methods are disclosed.

In one embodiment, the surgical compression instrument includes a pivot body attached with and extending longitudinally along a first implant support and including a receiver configured for disposal of a second implant support. The first implant support is engageable with a receiver of a fastener having a shaft fixed with vertebral tissue and the second implant support is engageable with a receiver of a fastener having a shaft fixed with vertebral tissue. The surgical compression instrument includes a slider and an actuator that is connected with the slider to translate the slider relative to the pivot body such that the slider is engageable with the second implant support such that the second implant support moves relative to the first implant support to compress the vertebral tissue.

In one embodiment, a surgical system is provided. The surgical system includes a first fastener having a shaft fixable with vertebral tissue. A first implant support is engageable with a receiver of the first fastener. A second fastener has a shaft fixable with vertebral tissue. A second implant support is engageable with a receiver of the second fastener. A member is disposed longitudinally along the first implant support to pivotably connect the implant supports. A part is movable relative to the member and engageable with the second implant support such that the second implant support moves relative to the first implant support to compress the vertebral tissue.

BRIEF DESCRIPTION OF THE DRAWINGS

The present disclosure will become more readily apparent from the specific description accompanied by the following drawings, in which:

FIG. 9 is a perspective view of components of one embodiment of a surgical system in accordance with the principles of the present disclosure;

FIG. 10 is a detail view of the components shown in FIG. 9;

DETAILED DESCRIPTION

Figure 1:
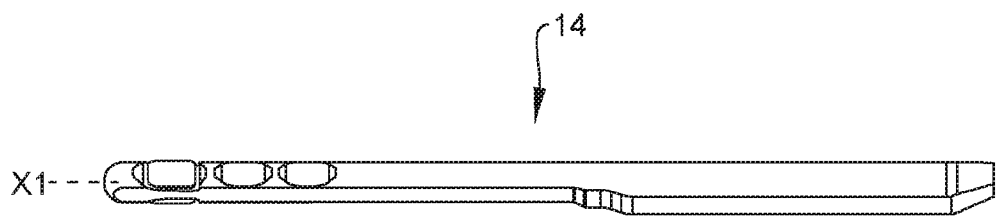
FIG. 1 is a perspective view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system includes surgical instruments that allow vertebral manipulation to treat spinal disorders, as described herein, for managing lordosis and/or kyphosis restoration. In some embodiments, the surgical instruments allow for parallel distraction and/or compression of vertebral tissue.

In some embodiments, the present surgical system includes a trauma instrument. In some embodiments, the present surgical system is utilized with a method to correct complex spinal deformities. In some embodiments, the present surgical system is utilized with a method to treat degenerative spinal disorders and/or employed with transforaminal lumbar interbody fusion procedures. In some embodiments, the present surgical system is configured for utilization with a sagittal adjusting screw (SAS), a fixed axis screw (FAS) and/or a multi-axial screw (MAS). In some embodiments, the present surgical system comprises a single distractor to treat degenerative spinal disorders, for example, for disposal along a side of vertebrae oriented for decompression and/or interbody cage insertion.

In some embodiments, the present surgical system includes a surgical instrument employed with a surgical method including degenerative lumbar spine fusion. In some embodiments, the present surgical system includes a surgical instrument employed with a surgical method including the step of segmental posterior stabilization with MAS screws. In some embodiments, the present surgical system includes a surgical method including an interbody fusion, posterior lumbar interbody fusion (PLIF), transforaminal lumbar interbody fusion (TLIF) utilizing a minimally invasive surgical approach or a percutaneous approach. In some embodiments, the present surgical system includes bone screw extenders, tissue retractors and a distractor/compressor system. In some embodiments, the present surgical system includes segmental distraction to facilitate decompression, including final construct compression. In some embodiments, the present surgical system includes radio transparent tissue retractor blades.

In some embodiments, the present surgical system includes a surgical instrument employed with a surgical method including the step of: connecting extenders, such as, for example, implant supports with MAS screws; connecting a sleeve with the implant support and the bone screw; and employing a universal screw driver for percutaneous implantation of the bone screw utilizing a PAK needle, guidewire or fluoroscopy. In some embodiments, the present surgical system includes screw based segmental distraction.

In some embodiments, the surgical system includes a compression instrument. In some embodiments, the compression instrument includes a member disposed longitudinally along a first implant support for pivotably connecting with a second implant support. In some embodiments, the compression instrument includes a slider being movable relative to the member and engageable with the implant supports such that the second implant support moves relative to the first implant support to compress the vertebral tissue. In some embodiments, the compression instrument includes connection buttons configured to prevent backing up of the compression instrument relative to the implant support. In some embodiments, the compression instrument is configured for one step top loading.

In some embodiments, the compression instrument includes an actuator, such as, for example, a threaded button for gradual activation of the slider. In some embodiments, the compression instrument includes a crossing point compatible with a pre-bent rod. In some embodiments, the slider is configured to drive compression of the vertebrae. In some embodiments, the compression instrument is utilized with a method including the steps of: removing a sleeve from an implant support; reducing a spinal rod with a first bone screw receiver; fixing a set screw with the bone screw receiver to fix the spinal rod in position and breaking off of a break off portion of the set screw; and engaging a second set screw with the second end of the spinal rod and a second bone screw receiver. In some embodiments, the bone screw receivers are compressed a selected distance apart. In some embodiments, the distance ranges from about 50 mm to about 19 mm. In some embodiments, the shafts of the bone screws are compressed at a relative angle. In some embodiments, the angle is in a range of about 27 degrees to about 8 degrees.

In some embodiments, the present surgical system includes a distractor configured for parallel distraction of selected vertebrae. In some embodiments, the distractor includes an adaptor engageable with the implant supports. In some embodiments, multi-axial bone screw receivers are utilized to facilitate connection of the implant supports with the adaptors.

In some embodiments, one or all of the components of the surgical system are disposable, peel-pack, pre-packed sterile devices used with a spinal construct. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis, kyphosis, and other curvature abnormalities, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including posterior and/or posterior mid-line and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior."

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are disclosed. Reference is made to the exemplary embodiments of the present disclosure, which are illustrated in the accompanying figures. Turning to FIGS. 1-4, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce instrumentation and/or components of spinal constructs at a surgical site within a patient body of a patient, for example, a section of a spine. In some embodiments, one or more of the components of surgical system 10 are configured for engagement with spinal constructs attached with vertebrae to manipulate tissue and/or correct a spinal disorder, such as, for example, a sagittal deformity, as described herein. In some embodiments, surgical system 10 may be employed with surgical procedures, such as, for example, corpectomy, discectomy and/or fracture/trauma treatment and may include fusion and/or fixation that employ implants to restore the mechanical support function of vertebrae.

Figure 3:
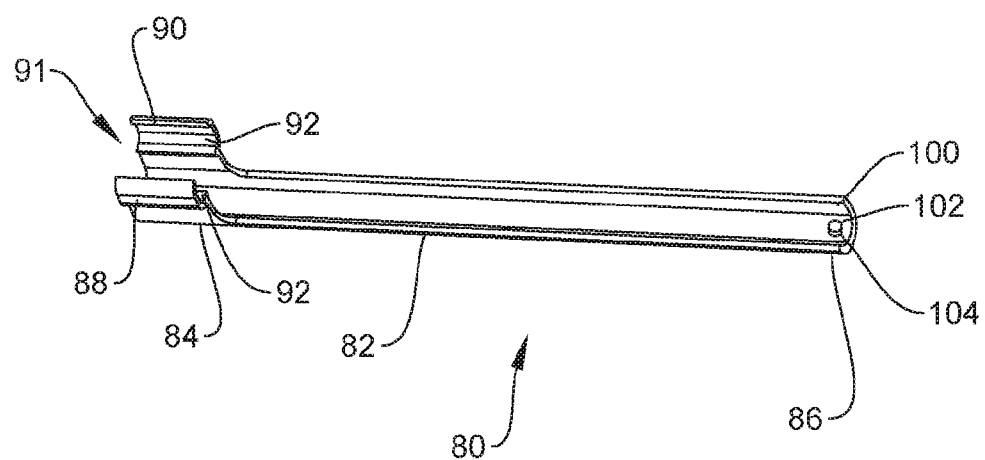
FIG. 3 is a perspective view of components of one embodiment of a surgical system in accordance with the principles of the present disclosure.
Figure 4:
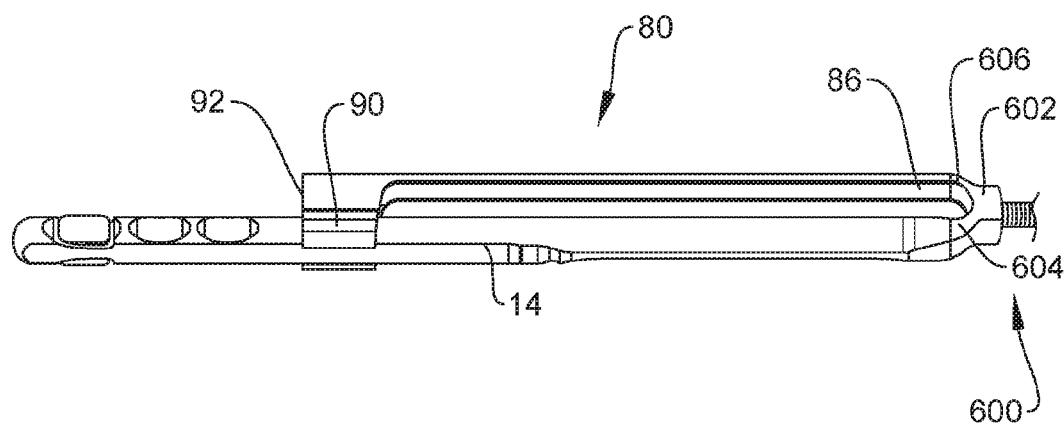
FIG. 4 is a perspective view of components of one embodiment of a surgical system in accordance with the principles of the present disclosure.
Figure 5:
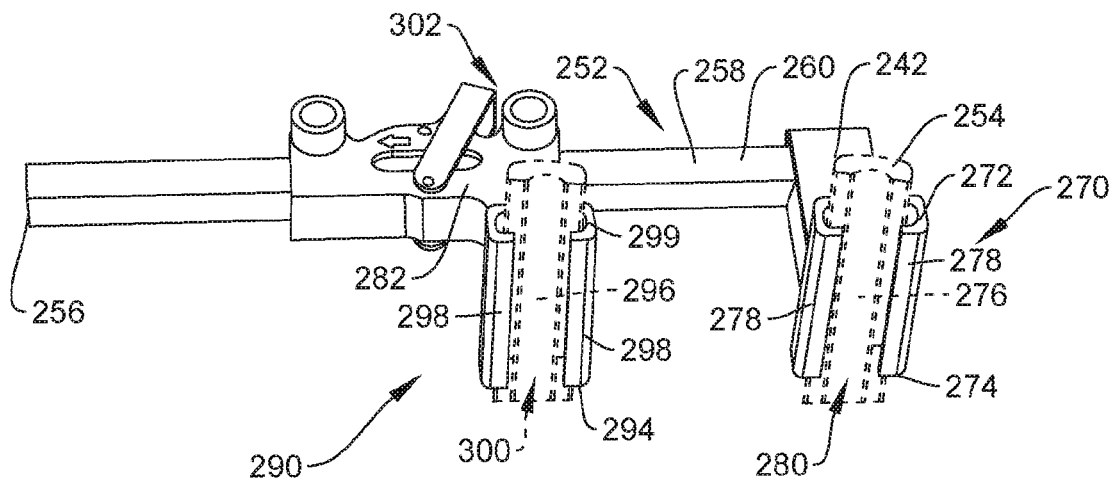
FIG. 5 is a break-away perspective view of components of one embodiment of a surgical system in accordance with the principles of the present disclosure.
Figure 6:
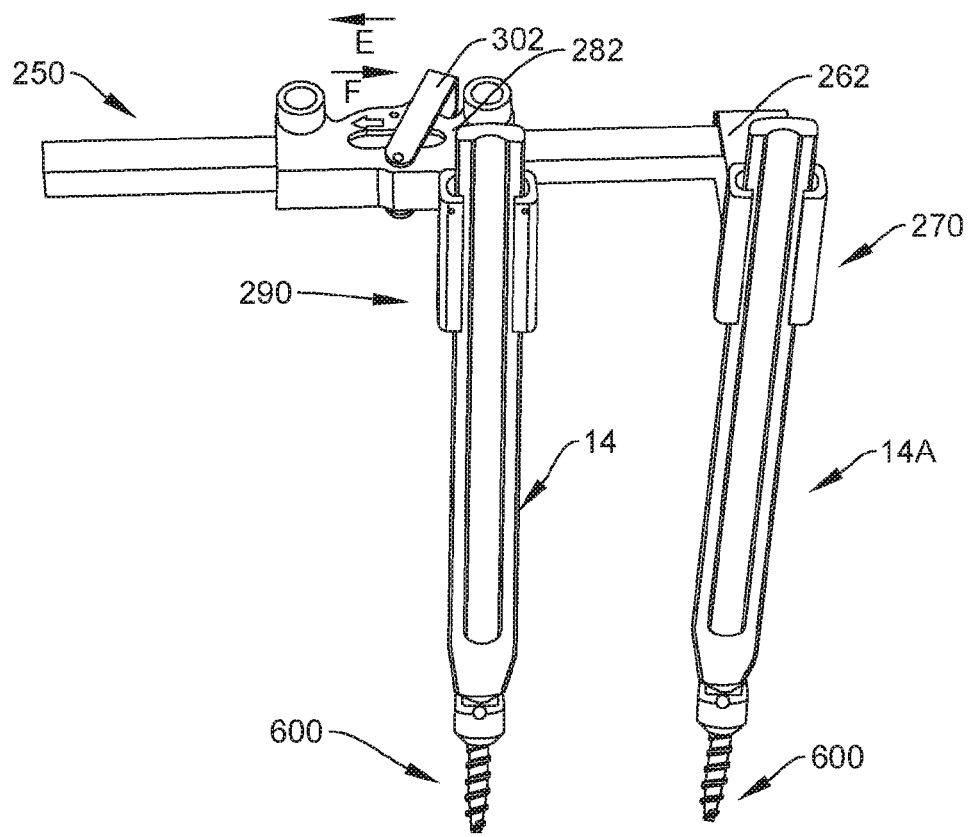
FIG. 6 is a perspective view of components of one embodiment of a surgical system in accordance with the principles of the present disclosure.
Figure 7:
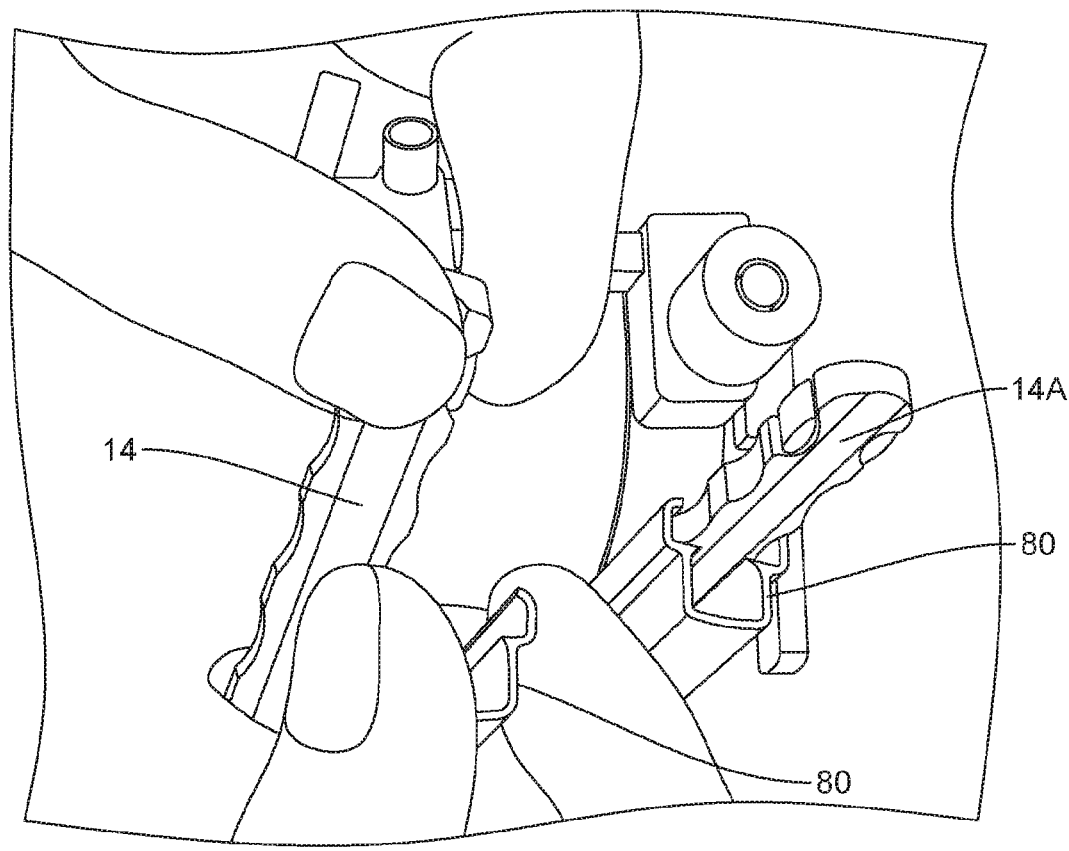
FIG. 7 is a perspective view of components of one embodiment of a surgical system in accordance with the principles of the present disclosure being handled by a user.

Surgical system 10 includes an extender, such as, for example, an implant support 14 and an implant support 14a (FIG. 6), similar to implant support 14, as described herein, and a sleeve 80 (FIG. 3), both engageable with separate and spaced apart bone screws 600 (FIGS. 4 and 6). Implant supports 14, 14a are connectable to surgical instruments, such as, for example, a distractor 250 (FIGS. 5 and 6) and/or a compression instrument 1000 to facilitate manipulation of tissue, as described herein.

Figure 2:
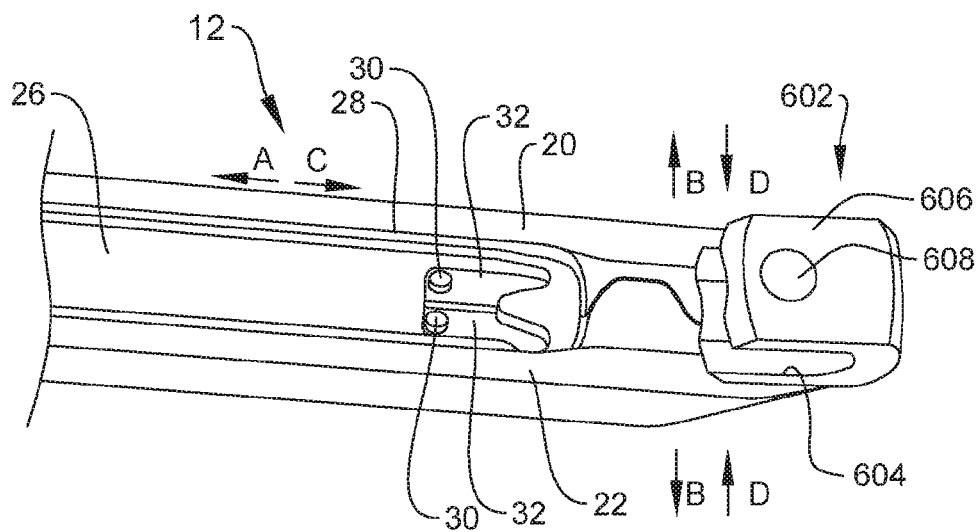
FIG. 2 is a break-away perspective view of components of one embodiment of a surgical system in accordance with the principles of the present disclosure.

Implant support 14 extends along an axis X1, as shown in FIG. 1. Implant support 14 includes a first extension 20 and a second extension 22, as shown in FIG. 2. Extensions 20, 22 are moveable relative to each other, via relative translation of a translation element, such as, for example, a slide 26 disposed with implant support 14, as shown in FIG. 2. Slide 26 is manipulated for translation within a channel 28 to move extensions 20, 22 between an open orientation and a closed, capture orientation. Slide 26 is translated, in a direction shown by arrow A in FIG. 2, to cause extensions 20, 22 to rotate and expand, in a direction shown by arrows B, to the open orientation. In the open orientation, pins 30, connected with extensions 20, 22, are disposed in a bottom of slots 32 of slide 26. Slide 26 is translated, in a direction shown by arrow C in FIG. 2, to cause extensions 20, 22 to rotate and contract, in a direction shown by arrows D, to the closed orientation to capture a wall 604 of a receiver 602 of bone screw 600, as shown in FIG. 2. In the closed orientation, pins 30 are disposed at the top of slots 32. In some embodiments, extensions 20, 22 are flexible to facilitate contraction.

Implant support 14 is connected with wall 604, as described herein in connection with FIGS. 3 and 4, so as to not block direct access to an implant cavity (between walls 604 and 606) of receiver 602 to facilitate insertion of an implant, such as a spinal rod, and perhaps also a securing device, such as a set cap or setscrew.

In some embodiments, one or more implant supports 14 are manipulable, as described herein, to provide a counter-torque for small deformity maneuvers and manipulation of vertebrae during a surgical treatment, for example, to displace, pull, twist or align vertebrae.

Referring again to FIGS. 3 and 4, sleeve 80 is connectable with implant support 14 and wall 606. Sleeve 80 includes a body 82 extending between a first end 84 and a second end 86. Body 82 extends along implant support 14. End 84 includes a first flange 88 and a second, opposing, flange 90 having corresponding mating surfaces defining a mating channel 91. Each surface may include a mating groove 92 formed therein. Mating grooves 92, or at least flanges 88, 90, are configured for disposal of a proximal portion of implant support 14, as shown in FIG. 4.

In various embodiments, flanges 88, 90 are flexible such that flanges 88, 90 snap fit around and into engagement with implant support 14. Upon disposal of implant support 14 with flanges 88, 90, sleeve 80 is disposed in a configuration to capture a wall 606 of receiver 602, as shown in FIG. 4.

End 86 includes a surface 100 that defines a mating surface 102. Surface 102 is configured for capture of wall 606. In various embodiments, surface 102 includes a distal projection 104 configured for engagement with a cavity 608 (FIG. 2) of wall 606 of receiver 602 to facilitate engagement.

With continued reference to FIG. 4, bone screw 600 includes a shaft 610 and receiver 602. Receiver 602 is moveable relative to shaft in a multi axial configuration. Receiver 602 is configured for engagement with implant support 14 and sleeve 80, as described herein. At least one of the walls 604, 606 includes a surface that defines cavity 608 (FIG. 2). Each cavity 608 can be used to facilitate connection with implant support 14 and/or sleeve 80, as described herein. Walls 604, 606 include an inner surface that defines a U-shaped passageway 612 for disposal of a spinal rod, as described herein. The inner surface of receiver 602 includes a thread form configured for engagement with a set screw.

In assembly, operation and use, surgical system 10, similar to the systems and methods described herein, is employed with a surgical procedure, for treatment of a spine of a patient including vertebrae V, as shown in FIGS. 8-19. Surgical system 10 may also be employed with surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Surgical system 10 is employed with a procedure for treatment of an applicable condition or injury of an affected section of a spinal column and adjacent areas within a body. For example, vertebrae V includes a vertebral level V1, a vertebral level V2 and a vertebral level V3, as shown in FIG. 19. Diseased and/or damaged vertebrae and intervertebral discs are disposed at vertebra V2 between vertebrae V1 and V3. In some embodiments, components of surgical system 10 are configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, surgical system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for implantation of components of surgical system 10. A preparation instrument (not shown) can be employed to prepare tissue surfaces of vertebrae V, as well as for aspiration and irrigation of a surgical region.

Pilot holes or the like are made in selected vertebrae V1 and V3 for receiving bone screws 600. Implant supports 14, 14a are engaged with wall 604 of receiver 602, as described herein. Sleeves 80 are engaged with wall 606 of receiver 602, as described herein. Mating grooves 88, 90 are engaged with implant support 14, as described herein. A driver 650 is disposed adjacent vertebrae V at a surgical site and is manipulated to drive, torque, insert or otherwise connect bone screw 600 with vertebrae.

A distractor 250, as shown in FIG. 5, is connected with implant supports 14, 14a, to allow for distraction of vertebrae V connected with bone screws 600. Distractor 250 includes a longitudinal element, such as, for example, a rack 252 extending between an end 254 and an end 256. Rack 252 is configured to connect adjacent implant supports 14, 14a. Rack 252 includes an outer surface 258 having a plurality of teeth, such as, for example, splines 260 engageable with an arm 282, as described herein. Rack 252 includes an arm 262 extending from end 254. In some embodiments, arm 262 is attached with rack 252 with, for example, with clips, hooks, adhesives and/or flanges.

Arm 262 includes a member, such as, for example, an adaptor 270 extending between an end 272 and an end 274. Adaptor 270 includes a surface 276 and walls 278 that defines a receiver 280 extending between ends 272, 274. Receiver 280 is configured for disposal of implant support 14a. Adaptor 270 includes a rectangular cross section configuration, as shown in FIG. 5. In some embodiments, all or only a portion of the cross section of adaptor 270 may have alternate cross section configurations, such as, for example, arcuate, closed, V-shaped, W-shaped, oval, oblong triangular, square, polygonal, irregular, uniform, non-uniform, offset, staggered, and/or tapered.

Rack 252 includes arm 282 that is axially translatable relative to arm 162. Arm 262 includes a member, such as, for example, an adaptor 290 extending between an end 292 and an end 294. Adaptor 290 includes a surface 296 and walls 298 that define a receiver 300 extending between ends 292, 294. Receiver 300 is configured for disposal of implant support 14. Adaptor 290 includes a rectangular cross section configuration, as shown in FIG. 5. In some embodiments, all or only a portion of the cross section of adaptor 290 may have alternate cross section configurations, such as, for example, arcuate, closed, V-shaped, W-shaped, oval, oblong triangular, square, polygonal, irregular, uniform, non-uniform, offset, staggered, and/or tapered.

For distraction, implant support 14 is disposed with adaptor 290 and implant support 14*a* is disposed with adaptor 270, as shown in FIG. 6. Bone screws 600 with multi-axial receivers 602 facilitate manipulation of implant supports 14, 14*a* for engagement with adaptors 270, 290. Rack 252 includes a latch 302 that is pivotable relative to arm 282 for disposal in a distraction position, as shown in FIG. 6. In the distraction position, latch 302 engages rack 252 to allow axial and/or incremental translation of arm 282 relative to arm 262/rack 252 and prevents axial translation of arm 282 relative to arm 262/rack 252, in an opposing direction. For example, latch 300 is pivotable to the distraction position, as described herein, to allow translation of arm 282, in the direction shown by arrow E in FIG. 6, and prevent translation of arm 282, in the direction shown by arrow F, relative to arm 262/rack 252. As such, distraction of vertebrae V1, V3, which are connected with implant supports 14, 14*a*, can be performed.

In some embodiments, a dilator (not shown) is inserted between implant supports 14, 14*a* into contact with bony anatomy and determine tissue depth. In some embodiments, a retractor blades (not shown) are translated along the dilator into engagement with the bony anatomy. The blades are disposed with tissue to form a surgical passageway to facilitate insertion of a spinal implant, such as, for example, an interbody spinal implant.

Figure 8:
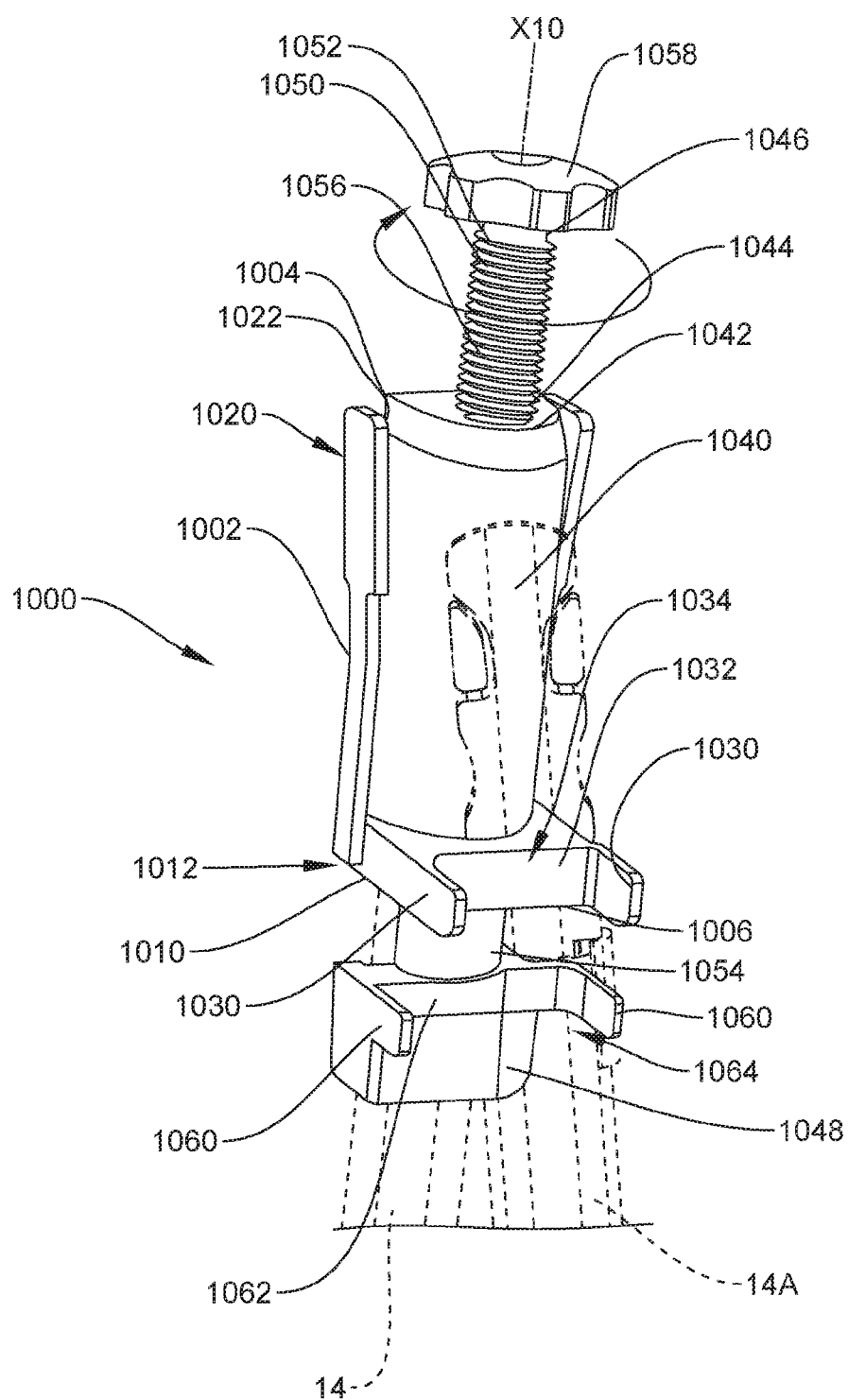
FIG. 8 is a break-away perspective view, partly in phantom, of components of one embodiment of a surgical system in accordance with the principles of the present disclosure.
Figure 12:
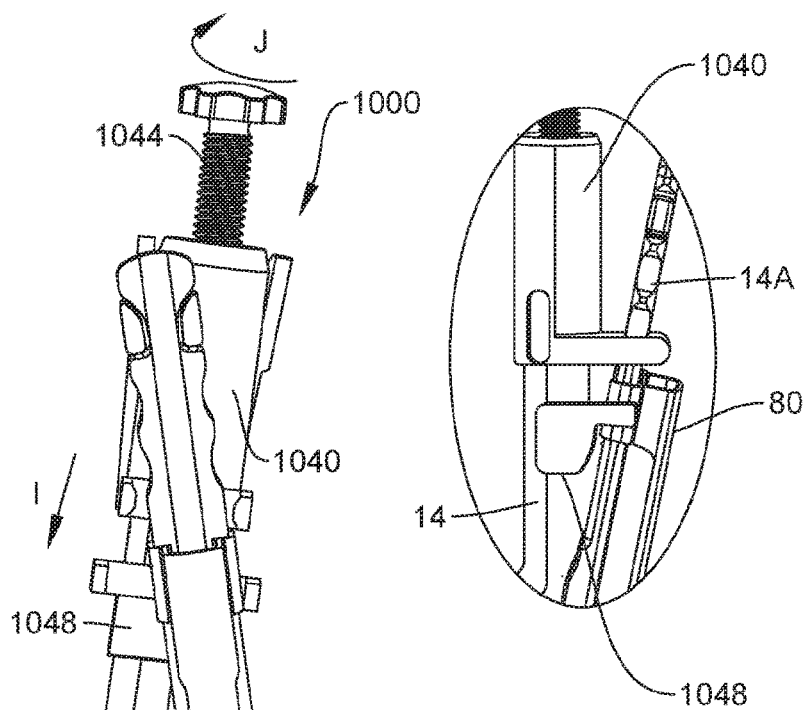
FIG. 12 is a detail view of the components shown in FIG. 11.
Figures 14, 15:
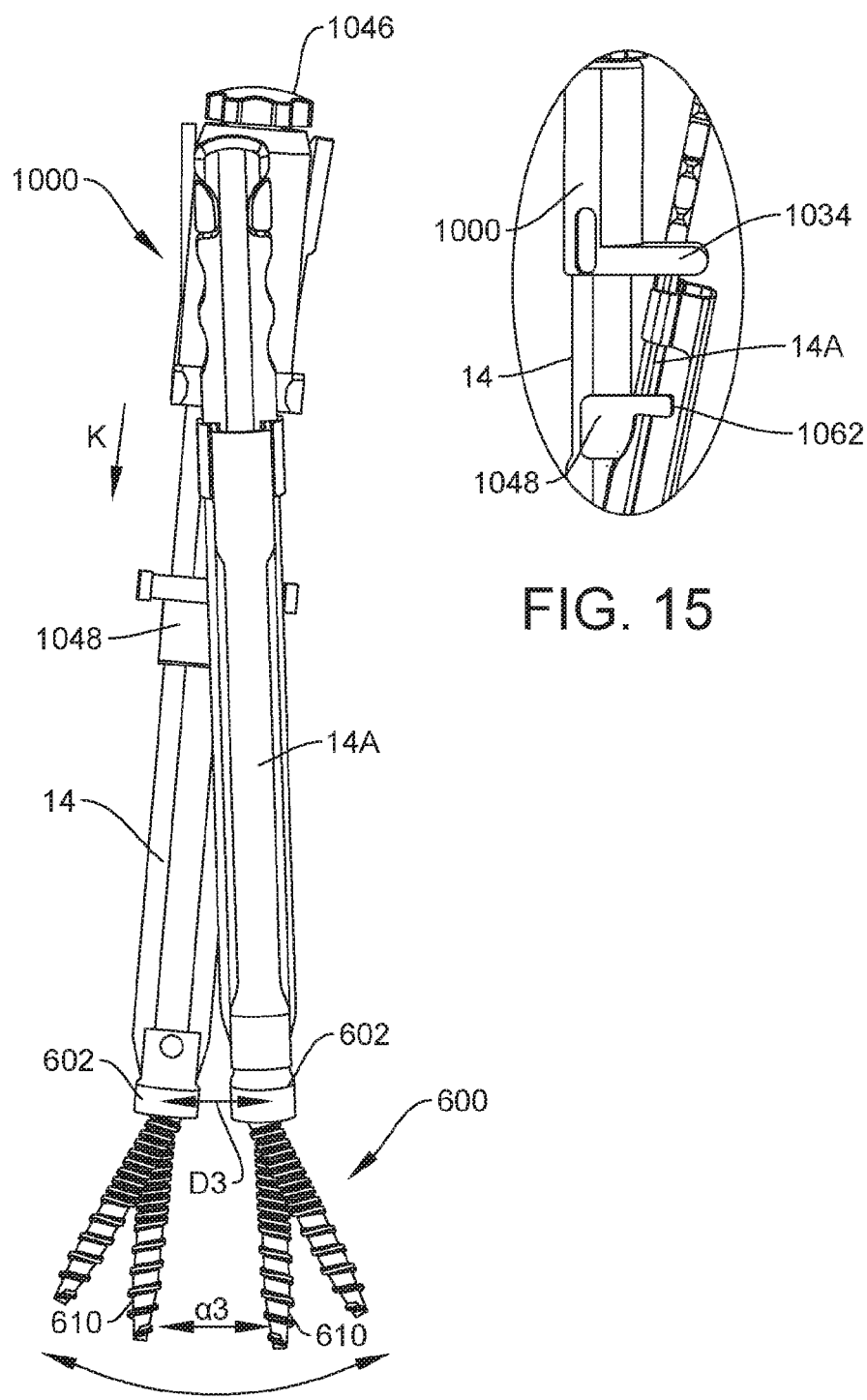
FIG. 14 is a perspective view of components of one embodiment of a surgical system in accordance with the principles of the present disclosure.
FIG. 15 is a detail view of the components shown in FIG. 14.

In some embodiments, a rod inserter (not shown) is engaged with a spinal rod 450 to direct and/or guide spinal rod 450 through implant supports 14, 14*a* into receiver 602. Sleeve 80 is disengaged from implant support 14, as shown in FIG. 14. A driver (not shown) is utilized to engage a set screw 601 with bone screw 600 to fix one end of spinal rod 450 disposed with bone screw 600 connected with implant support 14, as shown in FIG. 8.

Implant supports 14, 14*a* are crossed and a compression instrument 1000 is disposed with implant supports 14, 14*a*, as shown in FIGS. 8-11. Instrument 1000 is configured to facilitate compression of vertebrae V via connection with implant supports 14, 14*a*. Instrument 1000 includes a member, such as, for example, a pivot body 1002 configured to facilitate rotation of implant support 14*a* relative to body 1002. Body 1002 extends between an end 1004 and an end 1006 and defines an axis X10. Body 1002 includes a surface 1010 that defines a cavity, such as, for example, an opening 1012. Opening 1012 extends between end 1004 and end 1006. Opening 1012 is configured for disposal with a proximal end of implant support 14.

Body 1002 includes a lock, such as, for example a pair of depressible buttons 1020 configured connection with implant support 14. Buttons 1020 are disposable between a lock or locking orientation and a non-locking orientation. In the lock orientation, buttons 1020 releasably fix body 1002 with implant support 14. In the non-locking orientation, body 1002 is translatable and/or removable from implant support 14. Button 1020 may be spring biased to a locked position, such as by a projection 1022 defined by button 1020 being biased in the lock orientation into engagement with a groove 1024, shown in FIG. 13, of implant support 14 to releasably fix implant support 14 with body 1002. Buttons 1020 are configured to resist and/or prevent body 1002 from disengaging from implant support 14. In some embodiments, an outer surface of body 1002 includes one or a plurality of buttons 1020. In some embodiments, body 1002 may include ridges to facilitate gripping of body 1002, for example, to manipulate body 1002 relative to implant support 14, as described herein.

End 1006 includes arms 1030. Arms 1030 include a surface 1032 that define a receiver 1034. Arms 1030 extend transverse to axis X10. In some embodiments, arms 1030 may be variously oriented relative to axis X10, such as, for example, perpendicular, angular and/or offset. Receiver 1034 is configured for engagement with implant support 14*a*. In some embodiments, surface 1032 defines a cavity having a concave configuration to facilitate engagement with a surface of implant support 14*a* to facilitate crossing of implant support 14*a* with implant support 14. In some embodiments, receiver 1034 may include alternate configurations, such as, for example, arcuate, offset, staggered and/or angled portions.

Body 1002 includes a housing 1040. Housing 1040 includes a surface 1042 that defines an opening, such as, for example, a passageway 1044. Passageway 1044 is configured for moveable disposal of an actuator 1046 and a part, such as, for example, a slider 1048. Surface 1042 includes a thread form (not shown) engageable with actuator 1046 to facilitate translation of slider 1048, as described herein. Actuator 1046 includes a shaft 1050 that extends between an end 1052 and an end 1054. Shaft 1050 includes a threaded surface 1056 engageable with surface 1042 to facilitate translation. End 1052 includes a knob 1058 to facilitate rotation of actuator 1046. End 1054 includes slider 1048.

Slider 1048 includes arms 1060. Arms 1060 include a surface 1062 that define a receiver 1064. Arms 1060 extend transverse to shaft 1050. In some embodiments, arms 1060 may be variously oriented relative to shaft 1050, such as, for example, perpendicular, angular and/or offset. Receiver 1064 is configured for engagement with implant support 14*a*. In some embodiments, surface 1062 defines a cavity having a concave configuration to facilitate engagement with a surface of implant support 14*a*. Slider 1048 is actuated to translate along implant support 14 causing rotation of implant support 14*a* within receiver 1034 to facilitate compression of vertebrae. In some embodiments, receiver 1064 may include alternate configurations, such as, for example, arcuate, offset, staggered and/or angled portions.

To compress vertebrae V, body 1002 is translated over implant support 14, as shown by arrow G in FIG. 9, such that implant support 14 is disposed with opening 1012. Buttons 1020 snap into the lock position to fix instrument 1000 with implant support 14. Slider 1048 is disposed in an initial orientation such that receivers 1034, 1064 are disposed adjacent each other. Implant support 14*a* is disposed with receivers 1034, 1064, as shown in FIGS. 9 and 10, such that implant supports 14, 14*a* are captured by receivers 1034, 1064. In some embodiments, receivers 602 are disposed a relative distance D1. In some embodiments, distance D1 is about 50 mm. In some embodiments, shafts 610 are disposed at a relative angle α1. In some embodiments, angle α1 is about 27 degrees.

Actuator 1046 is rotated, as shown by arrow H in FIG. 9, causing threaded shaft 1050 to engage the threaded surface of housing 1040. Rotation of shaft 1050 causes slider 1048 to translate, in a direction shown by arrow I in FIGS. 11 and 12. Slider 1048 translates along implant support 14*a* causing further selective compression of vertebrae V. Receiver 1062 translates causing rotation of implant support 14*a* relative to instrument 1000. For example, receivers 602 are disposed a relative distance D2. In some embodiments, distance D2 is about 35 mm. In some embodiments, shafts 610 are disposed at a relative angle α2. In some embodiments, angle α2 is about 16 degrees.

Figure 11:
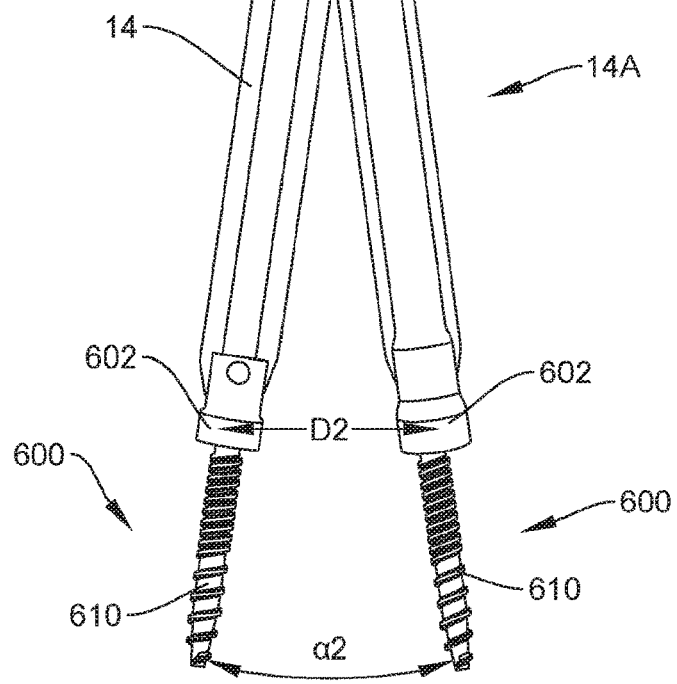
FIG. 11 is a perspective view of components of one embodiment of a surgical system in accordance with the principles of the present disclosure.
Figure 13:
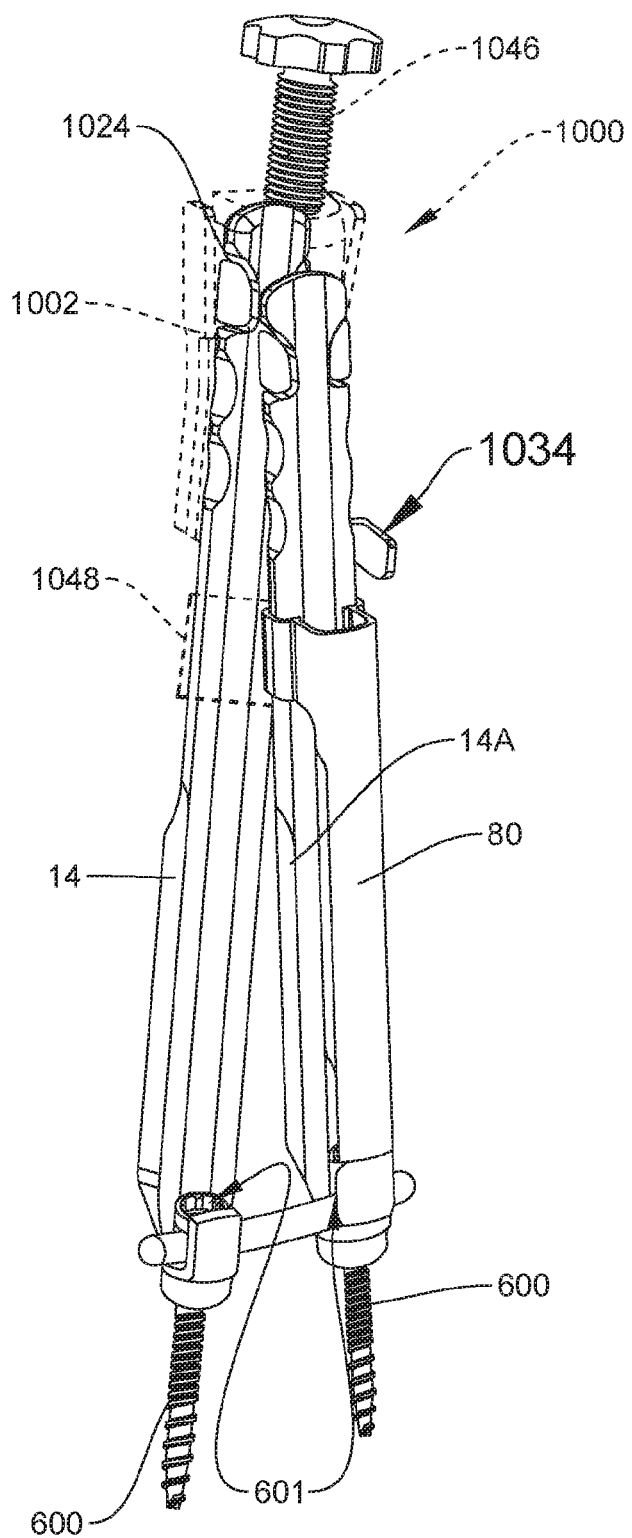
FIG. 13 is a perspective view, part in phantom, of components of one embodiment of a surgical system in accordance with the principles of the present disclosure.
Figure 16:
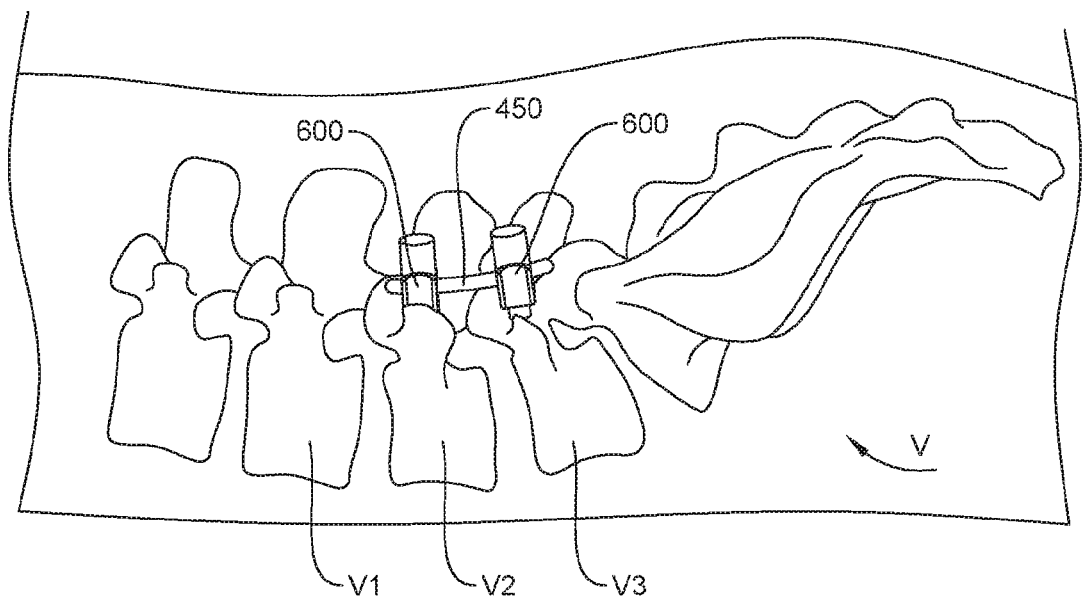
FIG. 16 is a side view of components of one embodiment of a surgical system in accordance with the principles of the present disclosure disposed with vertebrae.

Actuator 1046 is further rotated, as shown by arrow J in FIG. 11, causing threaded shaft 1050 to engage the threaded surface of housing 1040. Rotation of shaft 1050 causes slider 1048 to translate, in a direction shown by arrow L in FIGS. 14 and 15. Slider 1048 translates along implant support 14a causing selective compression of vertebrae V. Receiver 1062 translates away from receiver 1034 causing rotation of implant support 14a relative to instrument 1000. For example, receivers 602 are disposed a relative distance D3. In some embodiments, distance D3 is about 19 mm. In some embodiments, shafts 610 are disposed at a relative angle α3. In some embodiments, angle α3 is about 8 degrees. Compression instrument 1000 and implant supports 14 are removed, as shown in FIG. 16. Spinal rod is fixed with bone screws 600.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

In some embodiments, surgical system 10 includes one or a plurality of alternate surgical instruments, each configured for mating engagement in a quick release configuration with spinal constructs, as described herein. This configuration facilitates the interchangeability of the spinal constructs with the alternate surgical instruments. In some embodiments, surgical system 10 includes one or a plurality of alternate surgical instruments, such as, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical compression instrument comprising:
a body comprising a first opening, the body comprising first arms defining a first cavity, the body comprising a passageway positioned between the first opening and the first cavity, the first opening being configured for disposal of a first implant support, the first cavity being configured for disposal of a second implant support, the body being configured such that the first implant support is pivotably connected to the second implant support, the first implant support being engageable with a first receiver of a first fastener having a first shaft fixable with vertebral tissue and the second implant support being engageable with a second receiver of a second fastener having a second shaft fixable with vertebral tissue;
an actuator comprising a shaft having a first end disposed in the passageway and an opposite second end, the shaft of the actuator defining a longitudinal axis; and
a slider coupled to the second end and comprising a second opening configured for disposal of the first implant support, the slider comprising second arms defining a second cavity configured for disposal of the second implant support,
wherein rotation of the shaft of the actuator about the longitudinal axis translates the slider along the first implant support to rotate the second implant support within the second receiver and compress the vertebral tissue.

2. A surgical compression instrument as recited in claim 1, wherein the body includes opposite first and second sides, the first arms extending from the first side, the second side defining the first opening.

3. A surgical compression instrument as recited in claim 1, wherein rotation of the shaft of the actuator about the longitudinal axis does not rotate the slider about the longitudinal axis.

4. A surgical compression instrument as recited in claim 1, wherein the first end of the actuator is threaded and the second end of the actuator is non-threaded.

5. A surgical compression instrument as recited in claim 1, wherein the longitudinal axis is a first longitudinal axis, the first cavity defining a second longitudinal axis that extends through the second cavity.

6. A surgical compression instrument as recited in claim 1, wherein the longitudinal axis is a first longitudinal axis, the second cavity defining a second longitudinal axis that extends through the first cavity.

7. A surgical compression instrument as recited in claim 1, wherein the slider includes opposite first and second sides, the second arms extending from the first side, the second side defining the second opening.

8. A surgical compression instrument as recited in claim 1, wherein the first end of the shaft includes a threaded surface engageable with an inner surface of the body that defines the passageway to translate the slider relative to the body.

9. A surgical compression instrument as recited in claim 1, wherein the body includes a lock to releasably fix the body with the first implant support.

10. A surgical compression instrument as recited in claim 9, wherein the lock is movable between a lock orientation and a non-locking orientation and the lock is biased to the lock orientation.

11. A surgical compression instrument as recited in claim 9, wherein the lock includes a pair of depressible buttons configured for connection with the first implant support, the buttons each extending from one of the first arms.

12. A surgical compression instrument comprising:
a first implant support;
a second implant support
a pivot body comprising a first opening, the pivot body comprising first arms defining a first cavity, the body comprising a passageway positioned between the first opening and the first cavity, the first opening having the first implant support disposed therein, the first cavity having the second implant support disposed therein, the first implant support being engageable with a first receiver of a fastener having a shaft fixable with vertebral tissue and the second implant support being engageable with a second receiver of a fastener having a shaft fixable with vertebral tissue;

a slider comprising a second opening configured for disposal of the first implant support, the slider comprising second arms defining a second cavity having the second implant support disposed therein; and an actuator comprising a shaft having a first end disposed in the passageway and an opposite second end connected with the slider, the shaft of the actuator defining a longitudinal axis, wherein rotation of the shaft of the actuator about the longitudinal axis translates the slider along the first implant support to rotate the second implant support within the second receiver and compress the vertebral tissue.

13. A surgical system comprising:

a first fastener having a shaft fixable with vertebral tissue;

a first implant support that is engageable with a first receiver of the first fastener;

a second fastener having a shaft fixable with vertebral tissue;

a second implant support that is engageable with a second receiver of the second fastener such that the second implant support is axially translatable relative to the first implant support along a longitudinal axis defined by the implant supports;

a body comprising a first opening, the body comprising first arms defining a first cavity, the body comprising a passageway positioned between the opening and the first cavity, the first opening having the first implant support disposed therein, the first cavity having the second implant support disposed therein;

an actuator comprising a shaft having a first end disposed in the passageway and an opposite second end, the shaft of the actuator defining a longitudinal axis; and a slider comprising a second opening configured for disposal of the first implant support, the slider comprising second arms defining a second cavity having the second implant support disposed therein, wherein rotation of the shaft of the actuator about the longitudinal axis translates the slider along the first implant support to rotate the second implant support within the second receiver and compress the vertebral tissue, wherein rotation of the shaft of the actuator about the longitudinal axis translates the slider along the first implant support to rotate the second implant support within the second receiver and compress the vertebral tissue.

14. A surgical system as recited in claim 13, wherein the second implant support is disposed in the cavities as the slider translates along the first implant support.

15. A surgical system as recited in claim 13, wherein the first implant support is disposed in the openings as the slider translates along the first implant support.

16. A surgical system as recited in claim 13, wherein rotation of the shaft of the actuator about the longitudinal axis does not rotate the slider about the longitudinal axis.

17. A surgical system as recited in claim 13, wherein the longitudinal axis is a first longitudinal axis, the first cavity defining a second longitudinal axis that extends through the second cavity.

18. A surgical system as recited in claim 13, wherein the first end of the actuator is threaded and the second end of the actuator is non-threaded.

19. A surgical system as recited in claim 13, wherein the body includes a lock movable between a lock orientation and a non-locking orientation and the lock is biased to the lock orientation.

20. A surgical system as recited in claim 19, wherein the lock includes a pair of depressible buttons configured for connection with the first implant support, the buttons each extending from one of the first arms.

* * * * *